(12) United States Patent
Li et al.

(10) Patent No.: US 11,696,690 B2
(45) Date of Patent: *Jul. 11, 2023

(54) APPARATUS, SYSTEMS AND METHODS FOR CHARACTERIZING, IMAGING AND/OR MODIFYING AN OBJECT

(71) Applicant: The General Hospital Corporation, Boston, MA (US)

(72) Inventors: Li Li, Quincy, MA (US); Guillermo J. Tearney, Cambridge, MA (US)

(73) Assignee: The General Hospital Corporation, Boston, MA (US)

( * ) Notice: Subject to any disclaimer, the term of this patent is extended or adjusted under 35 U.S.C. 154(b) by 254 days.

This patent is subject to a terminal disclaimer.

(21) Appl. No.: 17/064,072

(22) Filed: Oct. 6, 2020

(65) Prior Publication Data

US 2021/0015370 A1    Jan. 21, 2021

Related U.S. Application Data

(63) Continuation of application No. 15/115,348, filed as application No. PCT/US2015/013893 on Jan. 30, 2015, now Pat. No. 10,813,555.

(Continued)

(51) Int. Cl.
*A61B 5/00* (2006.01)
*A61B 1/273* (2006.01)
(Continued)

(52) U.S. Cl.
CPC .......... *A61B 5/0095* (2013.01); *A61B 1/0615* (2013.01); *A61B 1/2733* (2013.01);
(Continued)

(58) Field of Classification Search
CPC ... A61B 5/0095; A61B 1/0615; A61B 1/2733; A61B 5/0071; A61B 5/0073;
(Continued)

(56) References Cited

U.S. PATENT DOCUMENTS 8,602,971 B2    12/2013 Farr
10,813,555 B2 *  10/2020 Li ..................... A61B 5/14551
(Continued)

FOREIGN PATENT DOCUMENTS

JP    2001178825    7/2001

OTHER PUBLICATIONS

International Search Report for International Application No. PCT/US2015/013893 dated Apr. 23, 2015.

(Continued)

*Primary Examiner* — Joel Lamprecht
(74) *Attorney, Agent, or Firm* — Quarles & Brady LLP (57) ABSTRACT

Method and apparatus can be provided according to an exemplary embodiment of the present disclosure. For example, with at least one first section of an optical enclosure, it is possible to provide at least one first electromagnetic radiation. In addition, with at least one second section provided within the enclosure, it is possible to cause, upon impact by the first radiation, a redirection of the first radiation to become at least one second radiation. Further, with at least one third section of the optical enclosure, it is possible to cause at least one second radiation to be provided to a tissue. For example, the redirection of the first radiation causes, at least approximately, a uniform optical illumination on of a surface of the tissue.

16 Claims, 5 Drawing Sheets

Related U.S. Application Data (60) Provisional application No. 61/933,669, filed on Jan. 30, 2014.

(51) Int. Cl.
*A61N 5/06* (2006.01)
*A61B 5/1455* (2006.01)
*A61B 5/1459* (2006.01)
*A61B 1/06* (2006.01)
*A61B 8/12* (2006.01)

(52) U.S. Cl.
CPC .......... *A61B 5/0071* (2013.01); *A61B 5/0073* (2013.01); *A61B 5/0075* (2013.01); *A61B 5/1459* (2013.01); *A61B 5/14551* (2013.01); *A61B 8/12* (2013.01); *A61N 5/062* (2013.01); *A61B 2562/146* (2013.01)

(58) Field of Classification Search
CPC . A61B 5/0075; A61B 5/14551; A61B 5/1459; A61B 8/12; A61B 2562/146; A61N 5/062
See application file for complete search history.

(56) References Cited

U.S. PATENT DOCUMENTS

| | | |
|---|---|---|
| 2011/0085721 A1 | 4/2011 | Guyon |
| 2011/0261367 A1 | 10/2011 | Gmitro |
| 2011/0275890 A1 | 11/2011 | Wang |
| 2011/0303015 A1 | 12/2011 | Ichihara |
| 2012/0328241 A1 | 12/2012 | Shishkov |
| 2013/0160559 A1 | 6/2013 | Ichihara |

OTHER PUBLICATIONS

International Written Opinion for International Application No. PCT/US2015/013893 dated Apr. 23, 2015.

Merman, M. et al. "Theoretical Analysis of Spectrally Encoded Endoscopy," Optics Express, vol. 17, No. 26, (Dec. 17, 2009).

\* cited by examiner

APPARATUS, SYSTEMS AND METHODS FOR CHARACTERIZING, IMAGING AND/OR MODIFYING AN OBJECT

CROSS-REFERENCE TO RELATED APPLICATIONS

The present application is a continuation of U.S. patent application Ser. No. 15/115,348 filed Jul. 29, 2016 which is a National Stage of International Application No. PCT/US2015/013893 filed Jan. 30, 2015 which relates to and claims priority from U.S. Provisional Patent Application Ser. No. 61/933,669 filed Jan. 30, 2014, which is incorporated herein by reference in their entirety.

FIELD OF THE DISCLOSURE

Various exemplary embodiments of the present disclosure relate generally to apparatus, systems and methods, which can characterize, image and/or or modify an object (e.g., tissue). In particular, various exemplary embodiments of the present disclosure can relate to apparatus, systems and methods for measuring photoacoustic signals. Further, various exemplary embodiments of the present disclosure relate to apparatus, systems and methods which can facilitate a low-risk assessment of cardiovascular function and diseases, such as, e.g., monitoring hemodynamic changes.

BACKGROUND INFORMATION

Use of light for characterizing, imaging and altering tissue has seen dramatically expansion during the last decade. A challenge for designing an optical device can be how to make an efficient use of light to generate a maximal diagnostic signal or treatment outcome. Further, many optical diagnosis and therapy are performed using endoscopes. The permissible optical fluence density on tissue surface can be regulated by laser safety standards. Thus, it is likely preferable to enlarge and/or homogenize the illumination to admit more optical power. However, it can be difficult to achieve a sufficient large uniform illumination area from a compact endoscope following the current paradigm, which uses light guides, lenses and mirrors.

Photoacoustic imaging is a radiological technology, which generates high-definition volumetric images of tissue by measuring light-induced sound waves —one or more photoacoustic signals—from its optically absorbing structures. Through exciting various biomolecules at their characteristic absorption wavelengths, photoacoustic signals can be used to analyze the molecular composition of a tissue at a clinically relevant depth. For example, through exploiting the differential absorption spectra of oxy- and deoxy-hemoglobin, photoacoustic signal, measured from blood at a plurality of selected optical wavelengths, can be used to evaluate local blood oxygenation of each individual blood vessel, and provide information regarding cancer biology and cardiovascular diseases. When optimizing a photoacoustic system, a major challenge can be how to maximize photoacoustic generation using finite optical exposure allowed by established safety standards.

Hemodynamic monitoring plays an important role in managing critically ill patients in emergency departments, surgical rooms and intensive care units. Adequate blood oxygen supply to tissue can be essential to sustain human life. A lasting deficiency of tissue oxygen could lead to the failure of vital organs, and is likely ultimately responsible for many deaths from a variety of diseases, such as, e.g., trauma, burn, heart attack and sepsis. Mixed venous oxygen saturation ($SvO_2$) is a preferred target of hemodynamic monitoring. $SvO_2$, the oxygen saturation measured from the mixed venous blood in a pulmonary artery, can reflect a dynamic balance between body's global oxygen supply and demand. Normally, $SvO_2$ is closely maintained between 60~80%. In patients, there are various challenges to the balance of oxygen metabolism. For example, the oxygen demand can increase in case of fever, shivering and/or seizure, while the oxygen supply can decrease when bleeding. When challenged, stable patients can restore the oxygen equilibrium by increasing the cardiac output, and do not require hemodynamic intervention.

However, in high-risk patients, especially those with a poor cardiopulmonary reserve, a compensatory increase in cardiac output can be limited. As a result, such patients have to call on bodies' last line defense by extracting more oxygen from blood, i.e., when $SvO_2$ starts to decrease. For example, an immediate intervention can be indicated if >10% deviation of $SvO_2$ from baseline is seen to last beyond, e.g., 3 minutes. In current practice, $SvO_2$ can be measured with an indwelling pulmonary artery catheter (PAC), introduced invasively from a peripheral vein. The use of the PAC was found to be associated with about 10% incidence of complications, including hematoma, vessel puncture and cardiac arrest. As a result, the use of the PAC has been significantly decreased, e.g., by 65% between 1993~2004.

Accordingly, there may be a need to address and/or overcome at least some of the issues of deficiencies described herein above.

Object and Summary of Exemplary Embodiments

To that end, apparatus, systems and methods according to certain exemplary embodiments of the present disclosure can be provided to overcome both aforementioned challenges by, e.g., increasing light-tissue interaction, thereby be utilized in broad applications in optical spectroscopy (e.g., scattering, fluorescence and Raman spectroscopy, etc.), imaging (e.g., photoacoustic imaging, diffuse optical tomography), or intervention (e.g., photodynamic, photothermal or low-level light therapy, etc.).

According to another exemplary embodiment of the present disclosure, apparatus, systems and methods for measuring a photoacoustic signal can be provided. Such exemplary apparatus, systems and methods can be utilized for measuring the photoacoustic signals using a light-integrating enclosure, which can safely increase light absorption in a targeted tissue, and generate a stronger photoacoustic signal for the detection. In still another exemplary embodiment of the present disclosure, apparatus, low-risk systems and methods can be provided so as to facilitate monitoring of the oxygen metabolism, e.g., in critical care. In addition, exemplary transesophageal photoacoustic endoscope, system and method according to a further exemplary embodiment of the present disclosure can be provided, which can be used to measure the photoacoustic signal from a pulmonary artery through a esophageal wall, and evaluate $SvO_2$ in, e.g., a less risky manner.

According to another exemplary embodiment of the present disclosure, apparatus, systems and methods can be provided to characterize, image and/or modify tissue with light (or other electro-magnetic radiation), which can include a source generating light, an optical integrating enclosure that performs (a) redirecting the light or other radiation to illuminate a tissue and (b) increasing of an optical fluence on a tissue surface. Such exemplary apparatus, systems and methods can be further configured to perform optical spectroscopy (e.g., scattering, fluorescence, Raman spectroscopy, etc.), imaging (e.g., photoacoustic imaging, diffuse optical tomography, etc.), and/or a treatment (e.g. photodynamic, photothermal or low-level light therapy, etc.).

In yet a further exemplary embodiment of the present disclosure, apparatus, systems and methods can be provided to measure the photoacoustic signal. For example, with a source, it is possible to generate light or other electromagnetic radiation with a time-varying intensity. In addition, using an optical integrating enclosure, it is possible to perform (a) redirecting of the light or other radiation to illuminate the tissue, and (b) increasing the optical fluence on the tissue surface. Further, with at least one acoustic transducer, it is possible to detect acoustic signals generated from the illuminated tissue volume.

According to yet another exemplary embodiment of the present disclosure, endoscopic apparatus, systems and methods can be provided for assessing cardiovascular functions or diseases, such as, e.g., monitoring a mixed venous oxygen saturation. For example, using the source, it is possible to generate light or other electro-magnetic radiation with a time-varying intensity. In addition, using an optical integrating enclosure, it is possible to redirect the light or the electro-magnetic radiation to illuminate a pulmonary artery or other cardiac tissue through a wall of an esophagus. Further, with at least one acoustic transducer, it is possible to detect acoustic signals generated from the pulmonary artery, and with a computer processing arrangement or unit, it is possible to determine at least one property of the pulmonary artery or other cardiac tissue.

Thus, method and apparatus can be provided according to an exemplary embodiment of the present disclosure. For example, with at least one first section of an optical enclosure, it is possible to provide at least one first electromagnetic radiation. In addition, with at least one second section provided within the enclosure, it is possible to cause, upon impact by the first radiation, a redirection of the first radiation to become at least one second radiation. Further, with at least one third section of the optical enclosure, it is possible to cause at least one second radiation to be provided to a tissue. For example, the redirection of the first radiation causes, at least approximately, a uniform optical illumination on of a surface of the tissue.

According to another exemplary embodiment of the present disclosure, the first section can have a cross-section that extends for a first extension, and the second section can have a cross-section that extends for a second extension. The first extension can be smaller than the second extension. The enclosure can be structured such that when at least one third radiation enters the enclosure from the tissue via the third section, the third radiation is deflected at at least one fourth section or at the second section within the enclosure, and forwarded back onto the surface of the tissue. The third radiation can be a return radiation from the tissue associated with the second radiation.

In addition, according to yet further exemplary embodiment of the present disclosure, an acoustic detector arrangement can be provided which is configured to receive an acoustic wave information from the tissue. The acoustic wave can be generated within the tissue in response to the second radiation provided on the tissue, the third radiation provided from the tissue, and/or at least one fourth radiation provided from the enclosure that is a redirected radiation of the third radiation within the enclosure. The enclosure can be composed of at least one material that allows most or entirety of the acoustic wave from the tissue to penetrate at least most of the enclosure. The enclosure can be provided in an approximate contact with the acoustic detector. Further, an acoustic matching layer can be provided between the acoustic detector and the enclosure.

According to still another exemplary embodiment, the first portion and/or the third portion can have a curvature that facilitates (i) a uniform distribution or (ii) a large area of illumination of at least one of the second radiation provided on the tissue, the third radiation provided from the tissue, and/or at least one fourth radiation provided from the enclosure that is a redirected radiation of the third radiation within the enclosure. The enclosure can have a shape of an acoustic lens. The second section can be (i) composed of a scattering material and/or (ii) have a scattering coating thereon, to effectuate the redirection of the first radiation. The scattering material can include a combination of an optically-transparent silicon rubber with light scattering particles. The enclosure can also comprise at least one fourth section through which the first radiation travels to reach the second section, where the fourth section can be approximately transparent. The transparent fourth section can be composed at least in part of silicon rubber, which can be substantially optically transparent.

In yet a further exemplary embodiment of the present disclosure, at least one fiber arrangement can be provided which can facilitate thereon or therethrough the first radiation. Further, an acoustical detector can be provided which is configured to receive an acoustic radiation from the tissue based on at least one of the second radiation provided on the tissue, the third radiation provided from the tissue, and/or at least one fourth radiation provided from the enclosure that is a redirected radiation of the third radiation within the enclosure. The enclosure, the fiber arrangement and the detector can be provided in a probe. The fiber arrangement can have a distal end in a proximity of the enclosure that has a curved shape to facilitate (i) a uniform distribution or (ii) a large area of illumination of the second radiation provided on the tissue, the third radiation provided from the tissue, and/or at least one fourth radiation provided from the enclosure that is a redirected radiation of the third radiation within the enclosure.

These and other objects, features and advantages of the exemplary embodiments of the present disclosure will become apparent upon reading the following detailed description of the exemplary embodiments of the present disclosure, when taken in conjunction with the appended claims.

BRIEF DESCRIPTION OF THE DRAWINGS

Further objects, features and advantages of the present disclosure will become apparent from the following detailed description taken in conjunction with the accompanying figures showing illustrative embodiments of the present disclosure, in which.

Throughout the figures, the same reference numerals and characters, unless otherwise stated, are used to denote like features, elements, components or portions of the illustrated embodiments. Moreover, while the subject disclosure will now be described in detail with reference to the figures, it is done so in connection with the illustrative embodiments. It is intended that changes and modifications can be made to the described exemplary embodiments without departing from the true scope and spirit of the subject disclosure as defined by the appended claims.

DETAILED DESCRIPTION OF EXEMPLARY EMBODIMENTS

Figure 1:
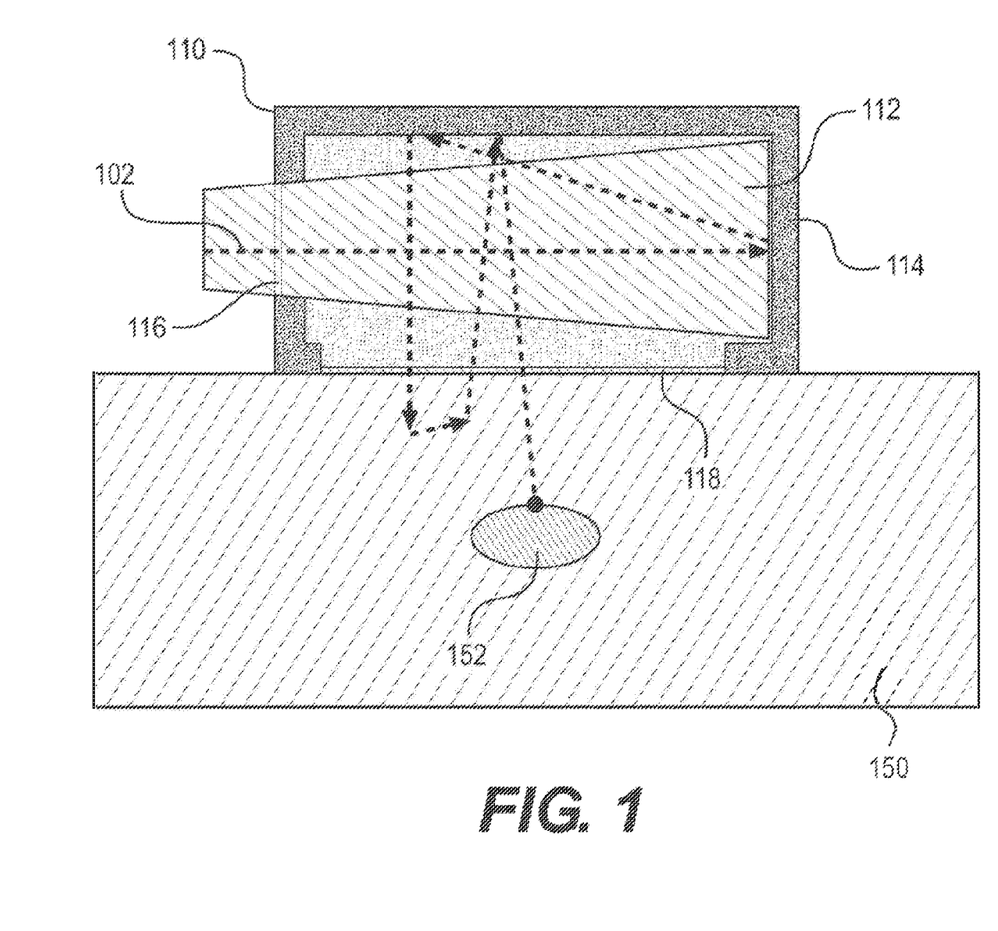
FIG. 1 is a cross-sectional side-view diagram of an optical apparatus according to an exemplary embodiment of the present disclosure.

FIG. 1 illustrates a cross-sectional view of an exemplary apparatus that includes an optical enclosure 110 according to one exemplary embodiment of the present disclosure. For example, light 102 (or other electro-magnetic radiation) can be delivered by the enclosure 110 to characterize, image and/or modify a targeted object 152 in a tissue 150. The enclosure 110 can include a light-transporting medium 112, a light-redirecting coating 114, an input port 116, and/or an output port 118. The light 102 (or other electro-magnetic radiation) can be provided into said the enclosure 110 via the input port 116, and exit to impact a surface of the tissue 150 through the output port 118. The light-transporting medium 112 can be composed of a material with a low optical absorption, such as, e.g., air, water, saline, oil, clear rubber, plastic and/or gel. The light-transporting medium 112 can also contain a small amount of optical scatters (e.g., <5% weight ratio), such as, e.g., titanium dioxide, hafnium oxide, zinc oxide, ytterbium oxide or hafium oxide particles.

The medium 112 can be surrounded by a light-redirecting coating 114, except at the input port 116 and/or the output port 118. The coating 114 can have a high optical reflectance, e.g., close to unity, and/or a near-Lambertian optical scattering phase function. The coating 114 can be composed of commercially available high diffusive reflectance material, such as, e.g., Spectralon, Spectraflect and/or Permaflect (Labsphere), and Avian-B or Avian-D white paint (Avian Technologies). Alternatively or in addition, the light-redirecting coating 114 can also be made by doping a medium with light scattering particles, such as, e.g., titanium dioxide, hafiium oxide, zinc oxide, ytterbium oxide and/or hafnium oxide, at a high concentration (e.g., >20% weight ratio). The coating 114 can also have a partial and/or high specular reflectance. After entering the enclosure 110, most of the light 102 or other electro-magnetic radiation can bounce around the enclosure 110, impact one or more surfaces of the coating 114, thereby become homogenized inside the medium 112. Such light 102 or radiation can only exits through either the output port 118 or the input port 116. In one exemplary embodiment, the output port 118 can have a larger area than the input port 116. Therefore, the optical enclosure 110 can redirect and/or expand most of the light 102 or other radiation to create a uniform wide-area illumination on a surface of the tissue 150 through the output port 118. Since a maximal permissible optical fluence density on the tissue surface is generally regulated by established safety standards, by enlarging and/or homogenizing the illumination, the enclosure 110 facilitates a delivery of a larger amount of optical energy onto the tissue 150. As an exemplary result, the interaction between the light 102 (or other radiation) and the target 152 can be increased. The input port 116 and/or the output port 118 can further be configured, shaped or constructed to have a desired curvature, e.g., in order to shape the light 102 (or other radiation) at the entrance and/or the exit to further homogenize and/or expand the illumination.

Furthermore, the enclosure 110 can be designed and/or modified to make a more efficient use of the same amount of the input light. Since the biological tissue is highly scattering to light, a significant portion of the light 102 (or other electro-magnetic radiation), which originally exits from the output port 118, is backscattered out from the tissue 150. The enclosure 110 can have a configuration to capture the re-emitted portion of the light 102 (through the input port 116 and/or the output port 118), send such light 102 (or other radiation) back through the output port 118 onto a surface of the tissue 150, so as to further increase the chance or an actuality of the interaction between the light 102 and the target 152. Therefore, the optical enclosure 110 can be used to further enhance a light-tissue interaction in various optical modalities, such as spectroscopies (e.g., scattering, fluorescence, Raman spectroscopy, etc.), imaging (e.g., photoacoustic imaging, diffuse optical tomography, etc.), or treatment (e.g., photodynamic, photothermal, low-level light therapy, etc.). Further, e.g., in order to obtain a uniform large-area optical illumination, the optical enclosure 110 can be shaped and or provided in a smaller size, e.g., when compared to other light-redirecting apparatus or systems that use only light guides, lenses or mirrors. Therefore, the exemplary enclosure 110 can be used in an optical endoscope system.

Figure 2:
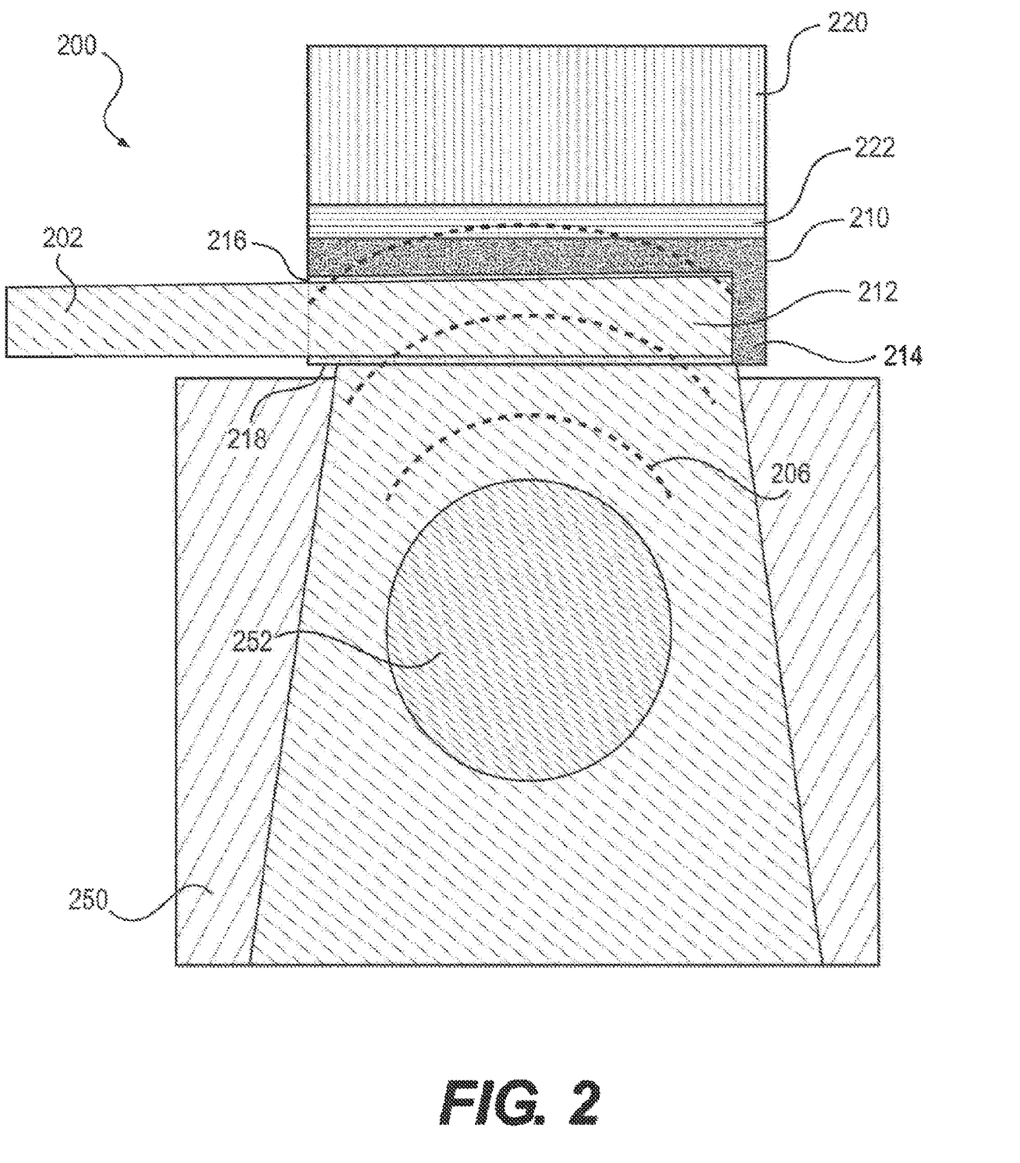
FIG. 2 is a cross-sectional side-view diagram of a photoacoustic measuring apparatus according to an exemplary embodiment of the present disclosure.

FIG. 2 illustrates a cross-sectional side-view diagram of a photoacoustic apparatus or device 200 according to an exemplary embodiment of the present disclosure. The exemplary photoacoustic device 200 can illuminate the tissue with light 202 or other electro-magnetic radiation, induce emission of an acoustic wave 206 from an optically absorbing object 252, such as, e.g., a blood vessel, within a tissue 250, record the light-induced sound remotely by an acoustic detector 220, and obtain information regarding the tissue by analyzing or reconstructing the recorded signals. The light 202 (or other radiation) can have a time-varying intensity. Examples of the acoustic detector 220 can include, but are not limited to, a microphone, a hydrophone, a piezoelectric transducer, a polyvinylidene fluoride film transducer, a capacitor micro-machined transducer, an optical acoustic sensor based on light interferometry, etc. The acoustic detector 220 can also be or include a combination of a plurality of aforementioned acoustic detectors, such as a phased array acoustic probe, etc. For example, a central frequency of the acoustic detector can preferably be in the range of about or exactly 0.5~100 MHz.

According to one exemplary embodiment of the present disclosure, the light 202 (or other radiation) can be delivered to the tissue 250 through a light-integrating enclosure 210. The light-integrating enclosure 210 can include a light-transporting medium 212, a light-redirecting coating 214, an input port 216, and an output port 218, etc. The medium 212 can be made of a material with a low light absorption, such as, e.g., air, water, oil, clear rubber, plastic and/or gel, etc. The medium 212 can be surrounded by the light-redirecting coating 214, e.g., except at the input port 216 and/or the output port 218. The coating 214 can have a high optical reflectance close to, e.g., unity and/or a near-Lambertian optical scattering phase distribution. The coating 214 can be composed of a commercially available high optical diffusive reflectance material, such as, e.g., Spectralon, Spectraflect or Permaflect (Labsphere), and Avian-B or Avian-D white paint (Avian Technologies). Alternatively or in addition, the light-redirecting coating 214 can also be made by doping a optically clear medium with light scattering particles, such as, e.g., titanium dioxide, hafnium oxide, zinc oxide, ytterbium oxide or hafnium oxide, at a high concentration (e.g. >20% weight ratio). As elaborated above, compared to a conventional photoacoustic device that utilizes a side illumination, the photoacoustic device 200 using a light-integrating enclosure 210 can produce a uniform illumination over a large surface of the tissue 250, thereby facilitate a use of more total optical energy, a re-use of the back-scattered light from tissue and an increase of the optical energy absorbed by the object 252, thereby boost the photoacoustic signal reaching the acoustic detector 220.

According to another exemplary embodiment of the present disclosure, the medium 212 and/or the light-redirecting coating 214 can further be made of a material having a low acoustic attenuation. Thus, the light-integrating enclosure 210 can act as an acoustic lens, and can be attached to the acoustic detector 220. Most of the acoustic wave 206 can be propagated through the light-integrating acoustic lens 210 to reach the acoustic detector 220. The low-acoustic-attenuation light-transporting medium 212 can be made of water, oil, poly(methyl methacrylate) (e.g., Arylic), polystyrene (e.g., Rexolite1422, C-lec Plastics), polymethylpentene (e.g., DX845, Mitsui Chemical), polyurethane, silicone rubber (e.g., RTV615, Momentive). The low-acoustic-attenuation light-redirecting coating can be made or otherwise generated by doping a medium, similar to that used to make the medium 212, with light scattering particles, such as, e.g., titanium dioxide, hafnium oxide, zinc oxide, ytterbium oxide or hafnium oxide, at a high concentration (e.g., >20% weight ratio). Furthermore, an acoustic matching layer 222 can be placed between the acoustic lens 210 and the acoustic detector 220, e.g., to reduce an acoustic loss due to the reflection. In addition or as an alternative, the lens 210 can be made of a material with a different acoustic speed than that of the tissue 250. To that end, the lens 210 can be shaped to diverge or converge the incoming acoustic wave 206, thereby facilitating a zoom-in or wide-angle view inside the tissue 250.

Figure 3:
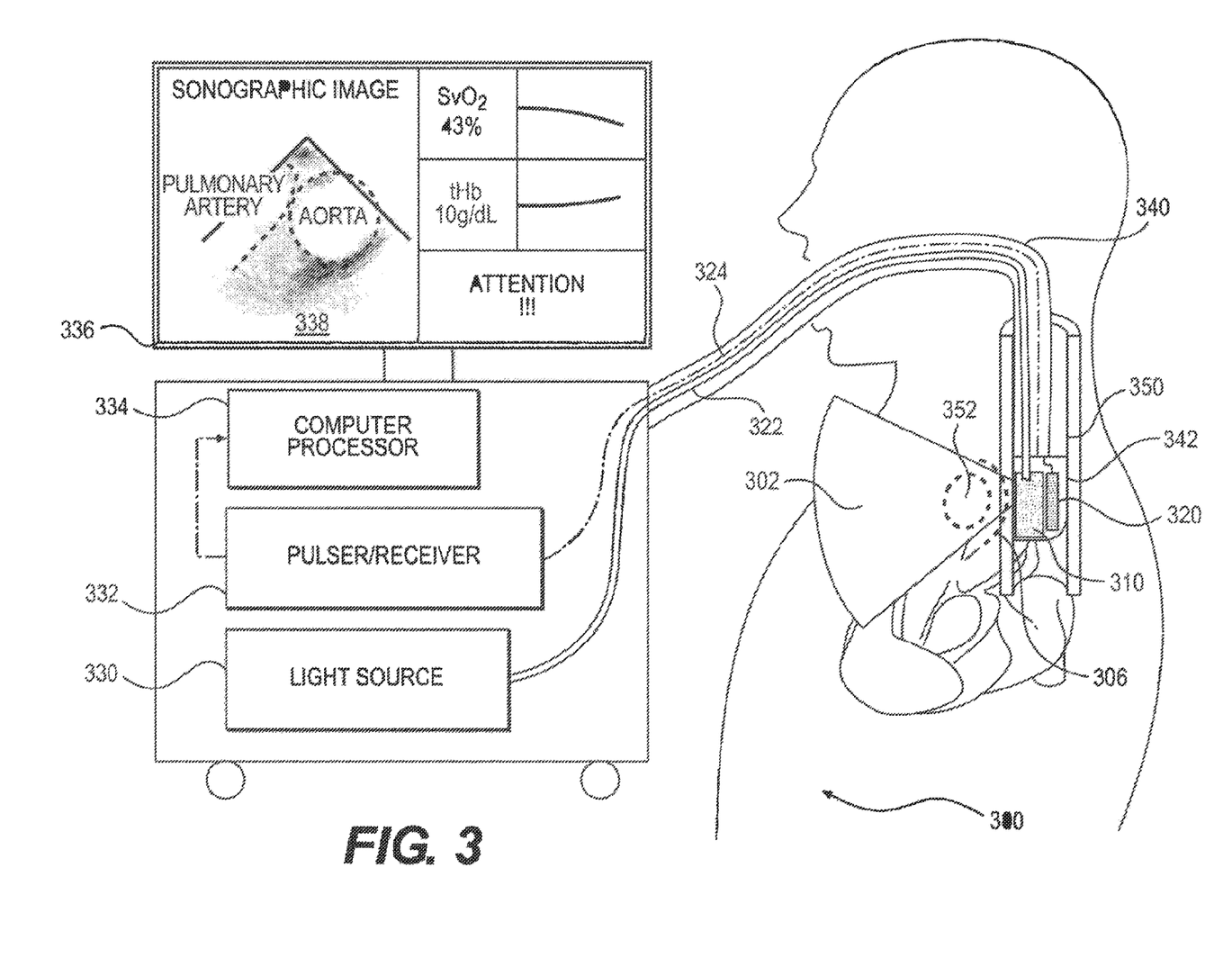
FIG. 3 is a diagram of a transesophageal photoacoustic endoscopic system for monitoring a mixed venous oxygen saturation, according to an exemplary embodiment of the present disclosure.

FIG. 3 illustrates a transesophageal photoacoustic endoscope system 300 according to another exemplary embodiment of the present disclosure. The exemplary system 300 can comprise an optical light source 330, a transesophageal probe (e.g., including a flexible shaft 340 and an inflexible in-esophagus head 342), an acoustic pulser/receiver 332, a processor 336 and a graphic user interface 338. The flexible shaft 340 can contain a segment of a light guide 322 and an electric cable 324. The inflexible head 342 can include a distal end of the light guide 322, a light-integrating acoustic lens 310 described herein, and an acoustic transducer 320. Either or both of the probe head 342 and the shaft 340 can have a diameter smaller than 15 mm, thereby facilitating an introduction thereof into the esophagus 308 through a mouth or a nose. Such exemplary system can be used to safely assess cardiovascular diseases and/or functions. For example, such exemplary system can be utilized to monitor mixed venous oxygen saturation ($SvO_2$) from a pulmonary artery 352 through a wall of an esophagus 350. Other examples of using such exemplary system include diagnosing atherosclerosis, assessing myocardial diseases, evaluating cardiac defects, guiding atrial ablation, etc.

The optical source 330 can generate a light 302 (or other electro-magnetic radiation) with a time-varying intensity. The light 302 (or other radiation) can have (but not limited to) a wavelength between, e.g., 600 and 1800 nm. The light source 330 can be or include a pulsed laser, such as a Q-switched Nd:YAG laser, a fiber laser, a dye laser, a Ti-sapphire laser, an OPO laser, or a pulsed diode laser. The pulse duration of the light 302 can be (but not limited to) at the order of nanoseconds. The source 330 can also be or include an intensity-modulated continuous-wave light source, such as a laser diode, a LED or a solid-state laser. The light guide 322 can be used to carry the light 302 from the source 330 into the head 342. Examples of such light guide 322 include, but are not limited to a borosilicate or silica/silica fiber bundle, a photonic crystal fiber, an articulated arm with mirrors or prisms, etc. The middle segment of the light guide 322 can be included inside the shaft, can contain loose fibers and be flexible. The light guide 322 can have inflexible segments close to at least one of the proximal end and the distal end, by fusing, gluing or adding a rigid housing to optical fiber(s). The light 302, generated by the optical source 330, can be focused by optical lenses into the proximal end of the light guide 322, exit from a distal end of said light guide 322, and provide the light 302 to the light-integrating acoustic lens 310. Then, the light 302 can be redirected to form a uniform wide-field illumination on a surface of the esophagus 350. The distal end of the light guide 322 can further be polished into a shape, which can deflect, reflect or diverge the light 302 to so as to achieve a large uniform optical illumination on the tissue.

According to an exemplary embodiment of the present, photoacoustic measurements can be made with the light at a plurality of wavelengths to evaluate a blood oxygen saturation, e.g., using one or more components described herein. For example, the source 330 can be tuned to generate the light with a plurality of wavelengths. In addition or alternatively, the source 330 can be or include a combination of a plurality of optical sources that can operate at distinct wavelengths. In addition, the shaft 340 and the head 342 can be configured, structured and/or sized to be navigated to characterize different tissue through the esophageal wall by advancing, rotating or flexing the drive shaft 340. In addition, the acoustic detector 320 can be rotated inside the probe head 340 to view the tissue in a view plane of interest. For an exemplary evaluation of $SvO_2$, as depicted in FIG. 3, a user can navigate the probe head 342 inside the esophagus 350 to obtain an appropriate good view of the pulmonary artery 352. After absorbing part of the light 302, the mixed venous blood inside a pulmonary artery 304 can emit an acoustic wave 306, which can be converted by an acoustic detector 320 into electrical signal. The electric signal can be carried by an electrical cable 324 into the acoustic pulser/receiver 332, where such electrical signal can be amplified, filtered and/or digitized. The digital samples of such signals can then be analyzed by a computer processor 334 to calculate or otherwise determine $SvO_2$ and analyze results, which can be provided thereby on a graphic interface 336. In addition, the pulser/receiver 332 can also be configured to transmit, e.g., a high-voltage electrical signal through the cable 324 to energize the acoustic transducer 320 to emit an acoustic wave (not shown). By detecting the reflected acoustic waves from tissue, real-time sonographic images 338 depicting tissue anatomy can be obtained and/or provided to guide a rapid deployment of the probe head 342.

Figure 4:
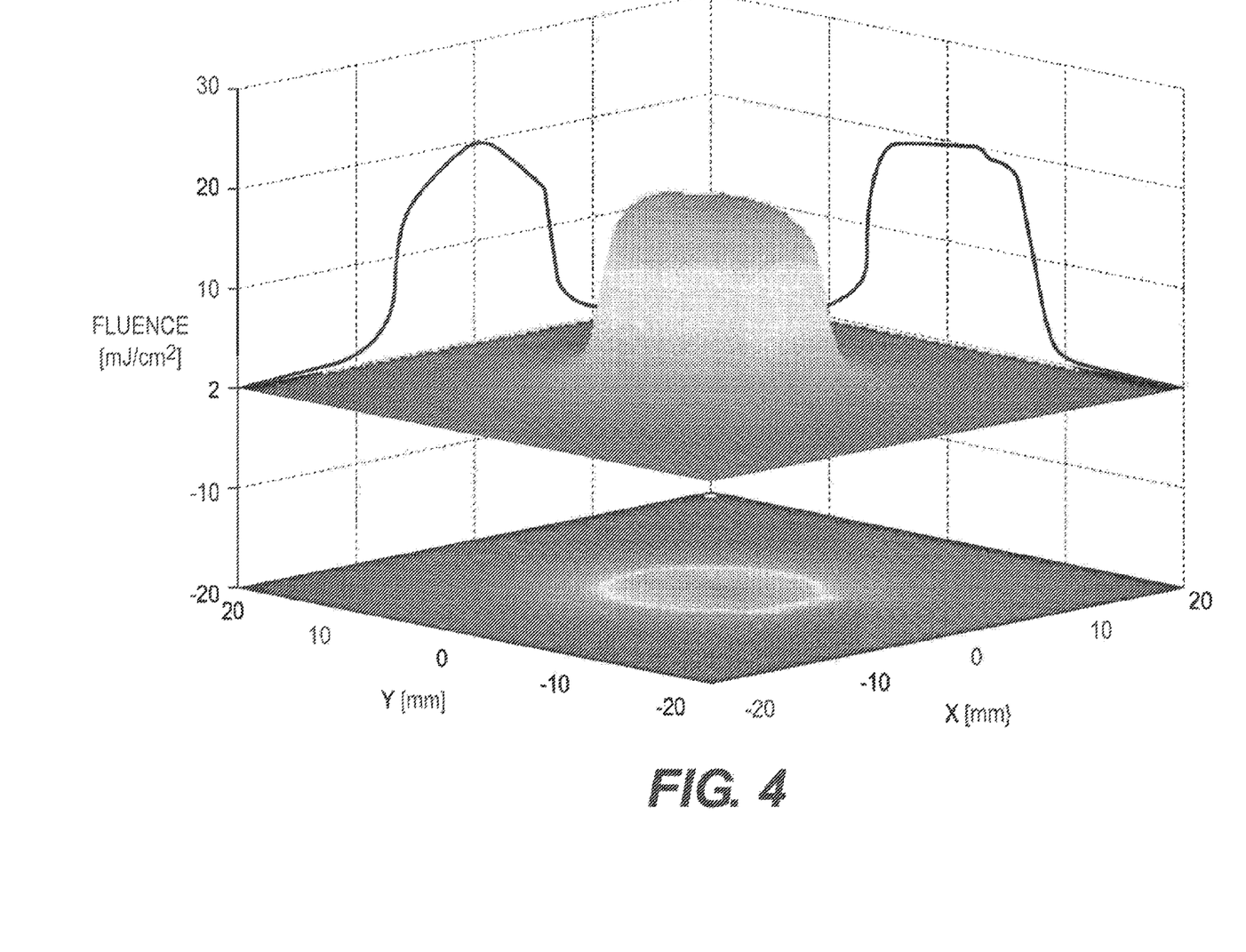
FIG. 4 is an exemplary wide-field optical illumination on tissue surface achieved by one exemplary embodiment of the apparatus, systems and methods according to the present invention illustrated in FIG. 3.

FIG. 4 shows a wide-field optical illumination on tissue surface achieved by the embodiment of the transesophageal photoacoustic endoscopic system according to the present disclosure illustrated in FIG. 3. For example, since the optical fluence density on tissue surface is regulated by laser safety standards, a wide-field illumination facilitates the use of more light to generate a higher photoacoustic signal. Simulation shows that, compared to a conventional photoacoustic endoscope where light is illuminated from a side of the acoustic detector, the exemplary transesophageal photoacoustic endoscopic system illustrated in FIG. 3 can produce more than twice of a photoacoustic emission. As shown in FIG. 4, a homogenous 13 mm-diameter illumination is obtained by the light-integrating acoustic lens 310 of a thickness of only 3 mm, which demonstrates the exemplary embodiments of the present disclosure can be useful for making compact endoscopes.

Figure 5:
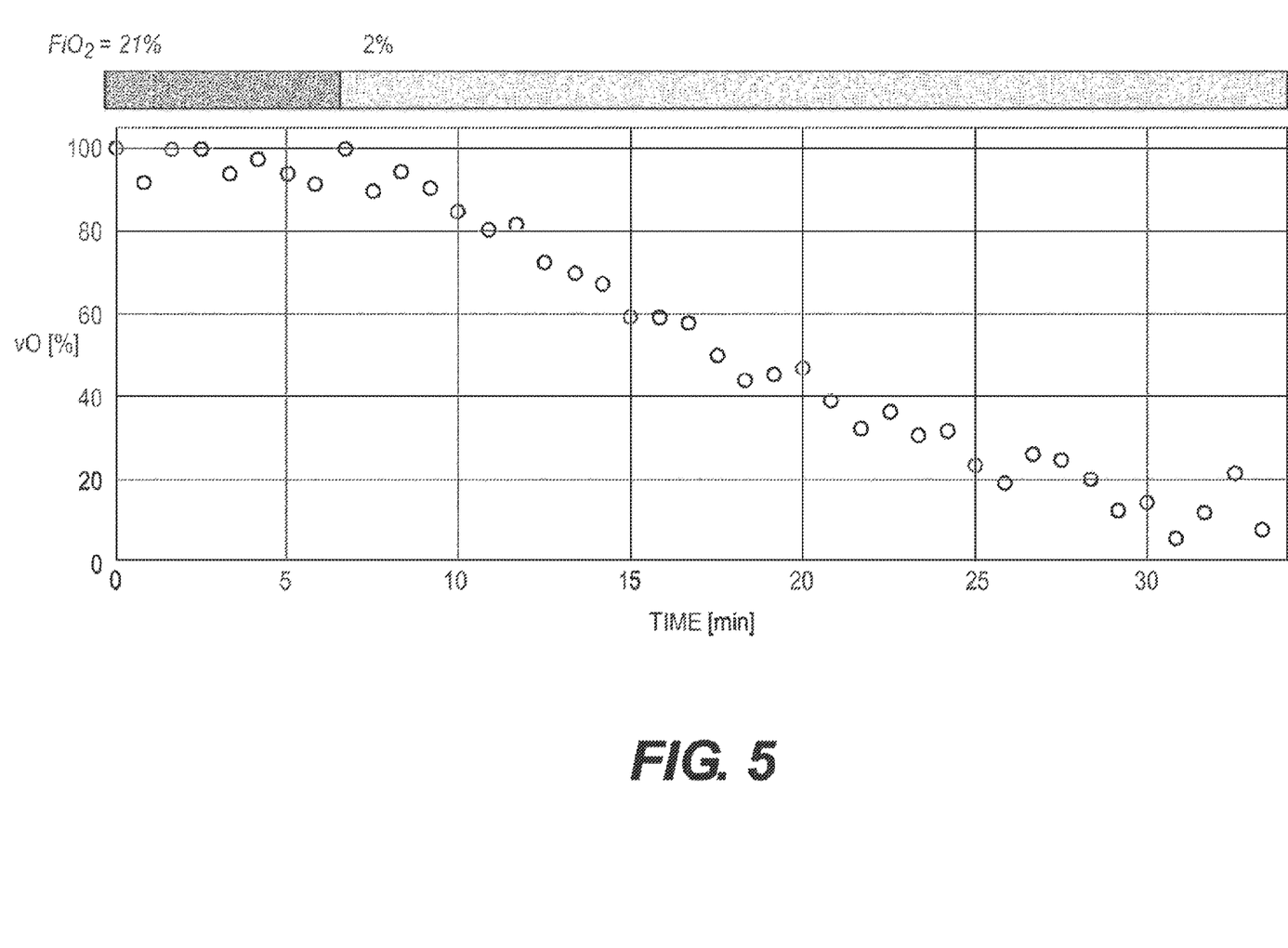
FIG. 5 is a graph illustrating a mixed venous oxygenation changes over time in response to varying fraction of inspired oxygen, evaluated by the transesophageal photoacoustic endoscope, according to the exemplary embodiment of the present disclosure illustrated in FIG. 3.

FIG. 5 shows a time profile of mixed venous oxygenation evaluated by the transesophageal photoacoustic endoscope according to the exemplary embodiment of the present disclosure. For example, blood can be circulated inside extracorporeal cardiopulmonary bypass circuit. Blood oxygen content can be modulated by varying the fraction of oxygen in the gas, which the blood breathes. The photoacoustic signals were measured from blood at two selected near-infrared wavelengths. The real-time oxygen saturation is estimated in the illustration of FIG. 4 based on the ratio of the two photoacoustic signals.

The foregoing merely illustrates the principles of the disclosure. Various modifications and alterations to the described embodiments will be apparent to those skilled in the art in view of the teachings herein. It will thus be appreciated that those skilled in the art will be able to devise numerous systems, arrangements and methods which, although not explicitly shown or described herein, embody the principles of the disclosure and are thus within the spirit and scope of the present disclosure. Further, the exemplary embodiments described herein can operate together with one another and interchangeably therewith. In addition, to the extent that the prior art knowledge has not been explicitly incorporated by reference herein above, it is explicitly being incorporated herein in its entirety. All publications referenced herein above are incorporated herein by reference in their entireties.

What is claimed is:

1. An apparatus, comprising:
an optical enclosure including a port, the optical enclosure including:
(i) at least one first section that facilitates a transmission therethrough of at least one first electro-magnetic radiation,
at least a portion of the at least one first electromagnetic radiation being transmitted adjacent to an opening of the port,
(ii) at least one second section within the optical enclosure that, upon impact by the first radiation, redirects the first radiation to become at least one second radiation,
at least a portion of the at least one second electromagnetic radiation being redirected through the opening of the port, and
(iii) at least one third section which is configured to provide the at least one second radiation to a tissue via the port,
wherein the redirection of the first radiation causes approximately uniform optical illumination onto a surface of the tissue; and
an acoustic detector to receive acoustic wave information from the tissue via the port in response to the optical illumination directed onto the surface of the tissue,
wherein a detection surface of the acoustic detector is adjacent to the optical enclosure and oriented parallel to both the surface of the tissue which receives the optical illumination and the opening of the port, and
wherein at least a portion of the acoustic wave information is emitted from the tissue toward the detection surface of the acoustic detector.

2. The apparatus according to claim 1, wherein the at least one first electro-magnetic radiation is not directed toward the opening of the port.

3. The apparatus according to claim 1, wherein the at least one first electro-magnetic radiation is not directed toward the detection surface of the acoustic detector.

4. The apparatus according to claim 1, wherein the first section has a cross-section that extends for a first extension, and the second section has a cross-section that extends for a second extension, and wherein the first extension is smaller than the second extension.

5. The apparatus according to claim 1, wherein the enclosure is structured such that when at least one third radiation enters the enclosure from the tissue via the third section, the third radiation is deflected at at least one fourth section or at the second section within the enclosure, and forwarded back onto the surface of the tissue, and wherein the third radiation is a return radiation from the tissue associated with the second radiation.

6. The apparatus according to claim 1, wherein the acoustic wave is generated within the tissue in response to at least one of the second radiation provided to the tissue, a third radiation provided from the tissue, or at least one fourth radiation provided from the enclosure that is a redirected radiation of the third radiation within the enclosure.

7. The apparatus according to claim 6, wherein the enclosure comprises at least one material that allows the acoustic wave from the tissue to penetrate the enclosure.

8. The apparatus according to claim 1, wherein the enclosure is provided in an approximate contact with the acoustic detector.

9. The apparatus according to claim 8, further comprising an acoustic matching layer provided between the acoustic detector and the enclosure.

10. The apparatus according to claim 1, wherein at least one of the first portion or the third portion has a curvature that facilitates (i) a uniform distribution or (ii) a large area of illumination of at least one of the second radiation provided on the tissue, a third radiation provided from the tissue, or at least one fourth radiation provided from the enclosure that is a redirected radiation of the third radiation within the enclosure.

11. The apparatus according to claim 1, wherein the second section at least one of:
(i) comprises a scattering material, or
(ii) has a scattering coating thereon,
to effectuate the redirection of the first radiation.

12. The apparatus according to claim 11, wherein the scattering material includes a combination of an optically-transparent silicon rubber with light scattering particles.

13. The apparatus according to claim 11, wherein the enclosure comprises at least one fourth section through which the first radiation travels to reach the second section, wherein the fourth section is approximately transparent.

14. The apparatus according to claim 13, wherein the transparent fourth section is composed at least in part of silicon rubber, which is substantially optically transparent.

15. The apparatus according to claim 1, further comprising:
   at least one fiber arrangement providing the first radiation; and
   wherein the acoustic detector is configured to receive the acoustic wave information from the tissue based on at least one of the second radiation provided on the tissue, a third radiation provided from the tissue, or at least one fourth radiation provided from the enclosure that is a redirected radiation of the third radiation within the enclosure, wherein the enclosure, the fiber arrangement, and the detector are provided in a probe.

16. The apparatus according to claim 15, wherein the fiber arrangement has a distal end in a proximity of the enclosure that has a curved shape to facilitate (i) a uniform distribution or (ii) a large area of illumination of at least one of the second radiation provided on the tissue, the third radiation provided from the tissue, or at least one fourth radiation provided from the enclosure that is a redirected radiation of the third radiation within the enclosure.

* * * * *

UNITED STATES PATENT AND TRADEMARK OFFICE
CERTIFICATE OF CORRECTION

PATENT NO. : 11,696,690 B2
APPLICATION NO. : 17/064072
DATED : July 11, 2023
INVENTOR(S) : Li Li et al.

Page 1 of 1

It is certified that error appears in the above-identified patent and that said Letters Patent is hereby corrected as shown below:

In the Specification

Column 5, Line 41, "hafium" should be --hafnium--.

Column 5, Line 53, "hafiium" should be --hafnium--.

Signed and Sealed this
Nineteenth Day of September, 2023

Katherine Kelly Vidal
*Director of the United States Patent and Trademark Office*